United States Patent
Branch et al.

(10) Patent No.: US 10,147,025 B2
(45) Date of Patent: Dec. 4, 2018

(54) VISUAL INDICATOR STATUS RECOGNITION

(71) Applicant: ShockWatch, Inc., Dallas, TX (US)

(72) Inventors: Clinton A. Branch, Jacksboro, TX (US); Angela K. Kerr, Plano, TX (US); Kevin M. Kohleriter, Dallas, TX (US)

(73) Assignee: ShockWatch, Inc., Dallas, TX (US)

(*) Notice: Subject to any disclaimer, the term of this patent is extended or adjusted under 35 U.S.C. 154(b) by 777 days.

(21) Appl. No.: 13/944,747

(22) Filed: Jul. 17, 2013

(65) Prior Publication Data

US 2014/0023264 A1    Jan. 23, 2014

Related U.S. Application Data

(60) Provisional application No. 61/672,421, filed on Jul. 17, 2012.

(51) Int. Cl.
*G06K 9/78* (2006.01)
*G01N 31/22* (2006.01)
*G06K 19/07* (2006.01)

(52) U.S. Cl.
CPC ............. *G06K 9/78* (2013.01); *G01N 31/229* (2013.01); *G06K 19/0717* (2013.01)

(58) Field of Classification Search
USPC ............ 116/216; 235/385; 292/92; 340/10.1, 340/545.2, 995.16, 540
See application file for complete search history.

(56) References Cited

U.S. PATENT DOCUMENTS

| | | | | |
|---|---|---|---|---|
| 4,785,286 A * | 11/1988 | Martin | ............... | E05B 65/1053 292/92 |
| 5,936,523 A * | 8/1999 | West | .................... | G08B 13/126 340/545.2 |
| 6,685,094 B2 | 2/2004 | Cameron | | |
| 7,243,007 B2 * | 7/2007 | Wilson | ................ | B60R 25/2009 340/995.16 |
| 7,262,792 B2 * | 8/2007 | Shniberg | .............. | G06K 7/1095 235/385 |
| 7,769,345 B2 * | 8/2010 | Johnson | ................. | G06K 9/228 235/462.2 |
| 8,120,467 B2 * | 2/2012 | Ehrman | ................. | G06Q 10/08 340/10.1 |
| 8,234,994 B1 | 8/2012 | Branch | | |
| 8,432,280 B2 * | 4/2013 | Conklin | .................... | B07C 3/00 340/540 |
| 8,757,503 B2 * | 6/2014 | Conzelmann | ............ | G01K 3/04 116/216 |
| 9,383,225 B2 * | 7/2016 | Bolick | ................... | G01D 4/008 |

(Continued)

*Primary Examiner* — Xuemei Chen
(74) *Attorney, Agent, or Firm* — James L. Baudino

(57) ABSTRACT

A system and technique for visual indicator status recognition includes an imaging system configured to capture a first optical data of an indicator, the imaging system configured to verify indicator code indicia is derivable from the first optical data. Responsive to verifying that the indicator code indicia is derivable from the first optical data, the imaging system is configured to capture a second optical data of the indicator. The system and technique also includes a detection module executable by a processing unit to analyze the second optical data and derive status information of the indicator.

20 Claims, 7 Drawing Sheets

(56) References Cited

U.S. PATENT DOCUMENTS

2009/0317002 A1* 12/2009 Dein .................. A61B 19/0256
382/224
2013/0007650 A1* 1/2013 Van Hoy ................... B64F 1/28
715/771

* cited by examiner

VISUAL INDICATOR STATUS RECOGNITION

BACKGROUND

During manufacturing, storage or transit, many types of objects need to be monitored due to the sensitivity or fragility of the objects. For example, some types of objects may be susceptible to damage if dropped or a significant impact is received. Other types of objects may need to be monitored for temperature conditions. Thus, for quality control purposes and/or the general monitoring of transportation conditions, it is desirable to determine and/or verify the environmental conditions to which the object has been exposed.

BRIEF SUMMARY

According to one aspect of the present disclosure, a system, method a computer program product for visual indicator status recognition is disclosed. The system and technique for visual indicator status recognition includes an imaging system configured to capture a first optical data of an indicator, the imaging system configured to verify indicator code indicia is derivable from the first optical data. Responsive to verifying that the indicator code indicia is derivable from the first optical data, the imaging system is configured to capture a second optical data of the indicator. The system and technique also includes a detection module executable by a processing unit to analyze the second optical data and derive status information of the indicator.

According to another embodiment of the present disclosure, a system for visual indicator status recognition includes a processing unit and a detection module executable by the processing unit to receive at least one image of an event detection indicator and analyze the at least one image to determine: identification information of the indicator; whether the indicator has been activated; and if activated, at least one characteristic of the activation based on the identification of the indicator.

According to yet another embodiment of the present disclosure, a system for visual indicator status recognition includes at least one image capture unit configured to capture a first optical data of an event indicator; a processing unit; and an imaging module executable by the processing unit to: analyze the first optical data to derive identification information of the event indicator; and based on the identification information, identify and display a capture window corresponding to the event indicator, the capture window configured to enable positioning of the event indicator within the capture window for capturing a second optical data of the event indicator, the capture window configured to locate at least one activation indicator of the event indicator within the second optical data.

BRIEF DESCRIPTION OF THE SEVERAL VIEWS OF THE DRAWINGS

For a more complete understanding of the present application, the objects and advantages thereof, reference is now made to the following descriptions taken in conjunction with the accompanying drawings, in which.

DETAILED DESCRIPTION

Figure 1:
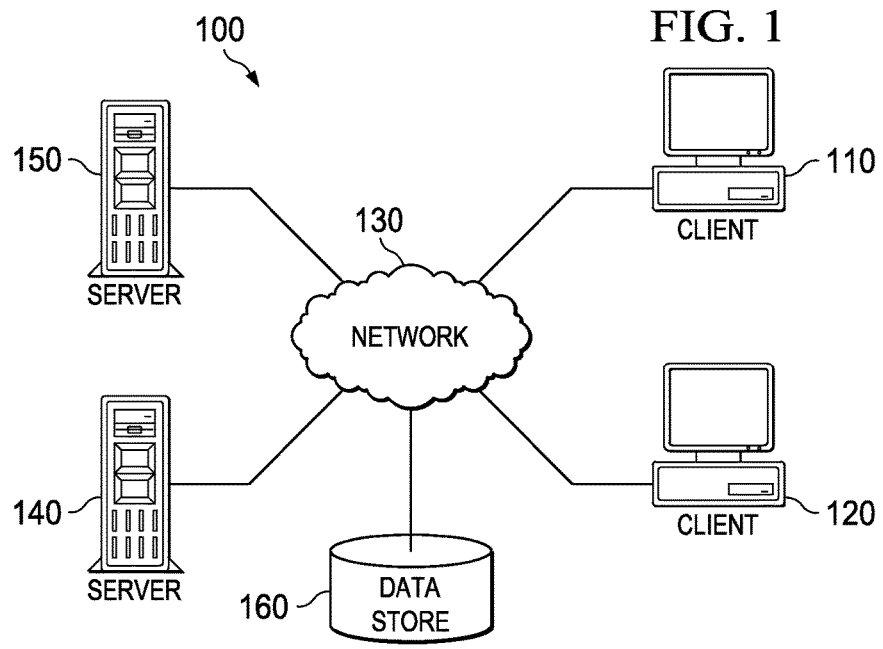
FIG. 1 is an embodiment of a network of data processing systems in which the illustrative embodiments of the present disclosure may be implemented.

Embodiments of the present disclosure provide a method, system and computer program product for visual indicator status recognition. For example, in some embodiments, the method and technique includes an imaging system configured to capture a first optical data of an indicator, the imaging system configured to verify indicator code indicia is derivable from the first optical data. Responsive to verifying that the indicator code indicia is derivable from the first optical data, the imaging system is configured to capture a second optical data of the indicator. The system and technique also includes a detection module executable by a processing unit to analyze the second optical data and derive status information of the indicator. Thus, embodiments of the present disclosure enable visual indicator status information to be captured/digitized to enable environmental conditions monitored by such indicator to be monitored/tracked and/or readily available to a customer or other entity. For example, in some embodiments, static and dynamic/variable status information may be derived from captured image/optical data of the indicator. The indicator information may be processed locally and/or remotely relative to the indicator.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer usable or computer readable medium(s) may be utilized. The computer readable medium may be a computer readable signal medium or a computer readable storage medium. A computer readable storage medium may be, for example but not limited to, an electronic, magnetic, optical, electromagnetic, infrared, or semiconductor system, apparatus, or device, or any suitable combination of the foregoing. More specific examples may include a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with and instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure as described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Figure 2:
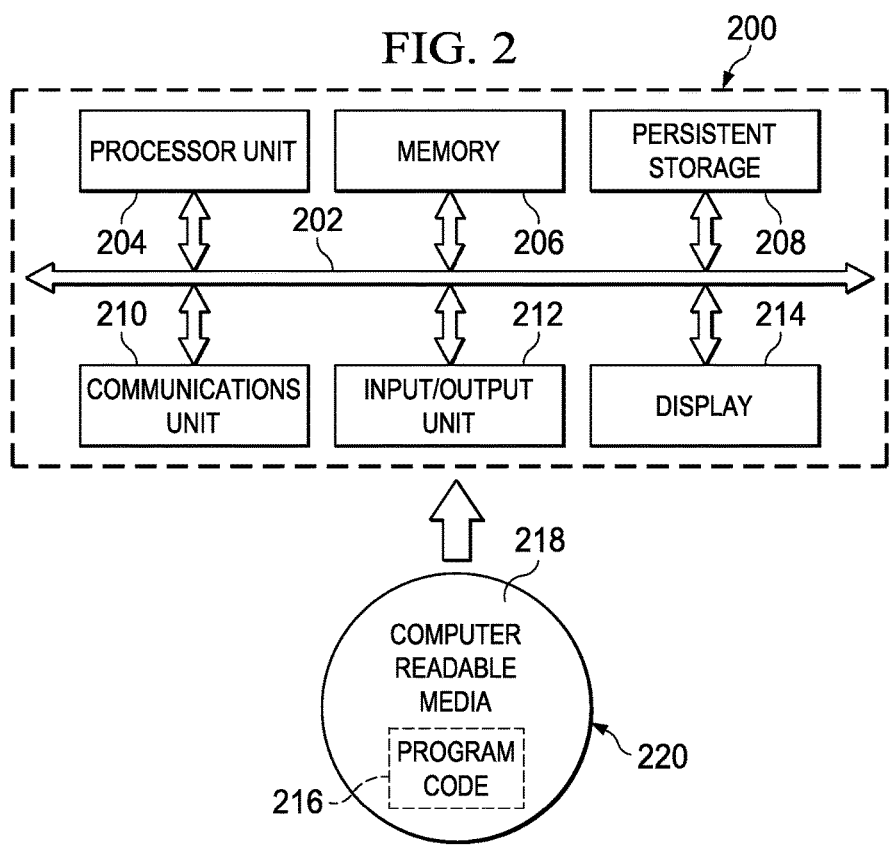
FIG. 2 is an embodiment of a data processing system in which the illustrative embodiments of the present disclosure may be implemented.

With reference now to the Figures and in particular with reference to FIGS. 1-2, exemplary diagrams of data processing environments are provided in which illustrative embodiments of the present disclosure may be implemented. It should be appreciated that FIGS. 1-2 are only exemplary and are not intended to assert or imply any limitation with regard to the environments in which different embodiments may be implemented. Many modifications to the depicted environments may be made.

FIG. 1 is a pictorial representation of a network of data processing systems in which illustrative embodiments of the present disclosure may be implemented. Network data processing system 100 is a network of computers in which the illustrative embodiments of the present disclosure may be implemented. Network data processing system 100 contains network 130, which is the medium used to provide communications links between various devices and computers connected together within network data processing system 100. Network 130 may include connections, such as wire, wireless communication links, or fiber optic cables.

In some embodiments, server 140 and server 150 connect to network 130 along with data store 160. In addition, clients 110 and 120 connect to network 130. Clients 110 and 120 may be, for example, personal computers or network computers. In the depicted example, server 140 provides data and/or services such as, but not limited to, data files, operating system images, and applications to clients 110 and 120. Network data processing system 100 may include additional servers, clients, and other devices.

In the depicted example, network data processing system 100 is the Internet with network 130 representing a worldwide collection of networks and gateways to communicate with one another. Network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

FIG. 2 is an embodiment of a data processing system 200 such as, but not limited to, client 110 and/or server 140 in which an embodiment of an access authentication system according to the present disclosure may be implemented. In this embodiment, data processing system 200 includes a bus or communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

In some embodiments, memory 206 may be a random access memory or any other suitable volatile or non-volatile storage device. Persistent storage 208 may take various forms depending on the particular implementation. For example, persistent storage 208 may contain one or more components or devices. Persistent storage 208 may be a hard drive, a flash memory, a rewritable optical disk, a rewritable magnetic tape, or some combination of the above. The media used by persistent storage 208 also may be removable such as, but not limited to, a removable hard drive.

Communications unit 210 provides for communications with other data processing systems or devices. In these examples, communications unit 210 is a network interface card. Modems, cable modem and Ethernet cards are just a few of the currently available types of network interface adapters. Communications unit 210 may provide communications through the use of either or both physical and wireless communications links.

Input/output unit 212 enables input and output of data with other devices that may be connected to data processing system 200. In some embodiments, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer readable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown. For example, a storage device in data processing system 200 is any hardware apparatus that may store data. Memory 206, persistent storage 208, and computer readable media 218 are examples of storage devices in a tangible form.

Figure 3:
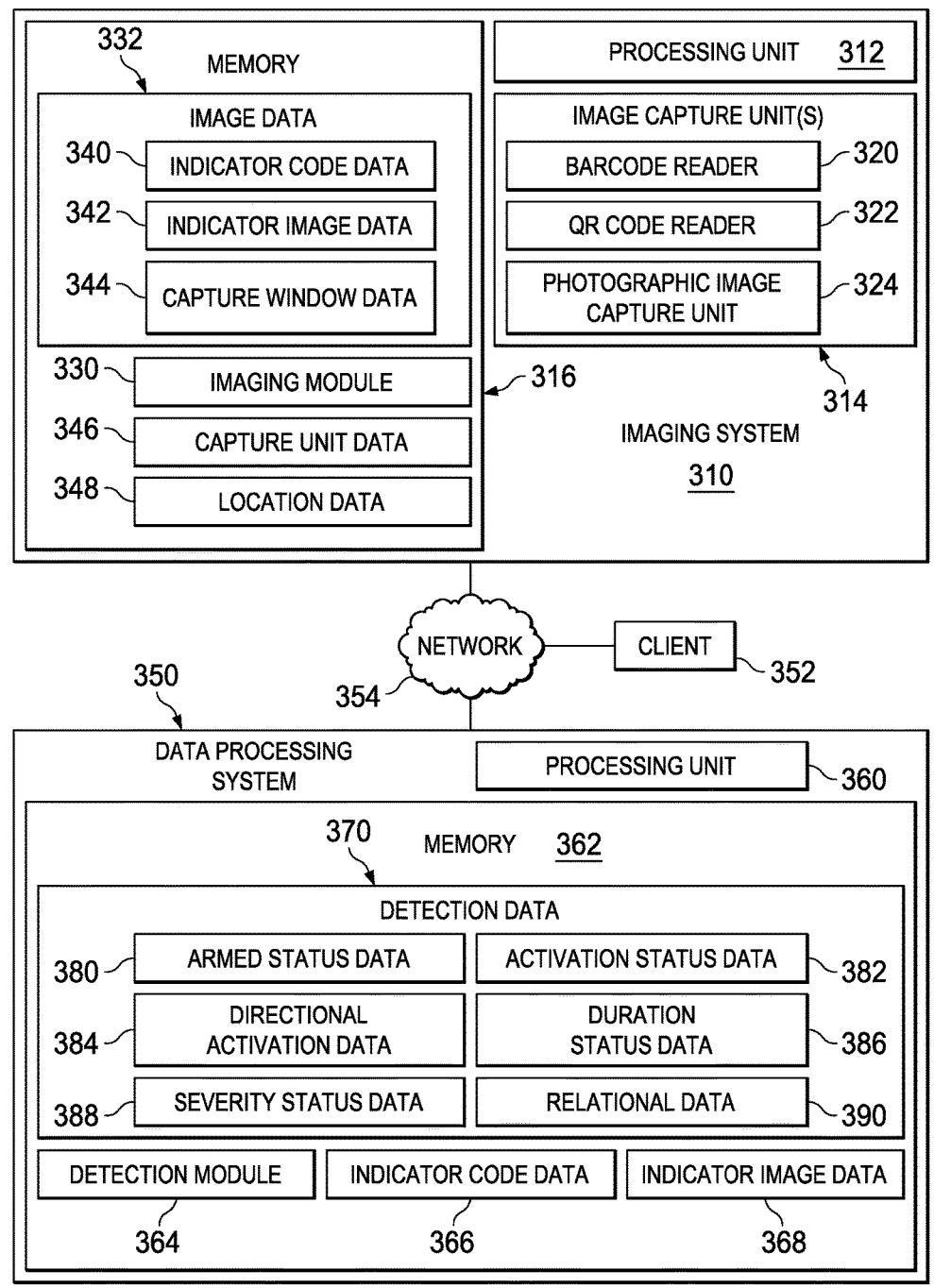
FIG. 3 is a diagram illustrating an embodiment of a data processing system in which illustrative embodiments of a visual indicator status recognition system according to the present disclosure may be implemented.

FIG. 3 is an illustrative embodiment of a system 300 for visual indicator status recognition. System 300 may be implemented on data processing systems or platforms such as, but not limited to, servers 140 and/or 150, clients 110 and/or 120, or at other data processing system locations. System 300 may be used with a variety of types of indictors (indicators and/or detectors that detect and display whether a particular monitored condition has occurred such as, but not limited to, impact indicators, tilt indictors and temperature indicators). In the embodiment illustrated in FIG. 3, system 300 comprises an imaging system 310 having a processing unit 312, one or more image capture units 314, and a storage resource or memory 316. Imaging system 310 may comprise any type of device capable of capturing image/optical information such as, but not limited to, a smartphone, a camera device, a tablet computing device, a notebook-type computing device, or any other type of portable or non-portable optical/imaging device. In the embodiment illustrated in FIG. 3, image capture units 314 include a barcode reader 320, a quick response (QR) code reader 322 and a photographic image capture unit 324. It should be understood that some types of image capture units may comprise multiple functionality. For example, photographic image capture unit 324 may be capable of capturing/reading QR codes. It should also be understood that, depending on the types of data/codes contained on a particular indicator, certain image capture units 314 may be omitted. For example, if the indicator does not contain barcodes, barcode reader 320 may be omitted. It should be further understood that other types of image capture units 314 may be used to optically capture and/or read certain types of indicia contained on particular indicators.

In the illustrated embodiment, memory 316 comprises an imaging module 330 and image data 332. In FIG. 3, imaging module 330 is illustrated as a software program residing in memory 316 and executable by processing unit 312. However, it should be understood that imaging module 330 may comprise software, logic and/or executable code for performing various functions as described herein (e.g., residing as software and/or an algorithm running on a processor unit, hardware logic residing in a processor or other type of logic chip, centralized in a single integrated circuit or distributed among different chips in a data processing system).

Imaging module 330 may be used to initiate and/or acquire image data 332 using one or more image capture units 314. Imaging module 330 may also be used to read and/or analyze the captured image data 332. For example, in some embodiments, imaging module may be used to perform text recognition to read/verify text-based indicia located on a particular indicator. In some embodiments, imaging module may be used to automatically acquire one type of image data in response to receiving/capturing another type of image data. For example, in some embodiments, system 310 may be configured such that, after capturing image data corresponding to a serial and/or model number of an indicator (e.g., via a barcode, QR code, text recognition from a captured photographic image, etc.), imaging module 330 may be configured to automatically capture/acquire a photographic image of the indicator (e.g., an image acquiring and/or focusing on a different portion of the indicator or a larger viewable area of the indicator). In some embodiments, imaging module 330 may be configured such that the subsequently acquired photographic image is captured/acquired after the indicator is "boxed" or located within a particular centering or image capture window (e.g., an image capture window or zone overlayed and/or viewable within a viewfinder or otherwise available within an optical imaging sensing device) to ensure that select areas of interest of the indicator are captured in the image. In some embodiments, depending on the serial and/or model number captured/read from one image, an image capture window may be used/selected based on such serial/model number (e.g., corresponding to the shape of the indicator and/or based on the areas of interest of such indicator). It should also be understood that in some embodiments, the order and/or sequence of particular types of image/optical data may be reversed and/or otherwise modified.

In the illustrated embodiment, image data 332 includes indicator code data 340, indicator image data 342 and capture window data 344. Indicator code data 340 may comprise information corresponding to code indicia captured/acquired from an indicator (e.g., via barcode reader 320, QR code reader, 322, etc.). The code indicia may comprise information associated with a serial number, model number or other type of code identifying a particular indicator. The code indicia may be derived from a barcode, QR code, derived based on text recognition processing, or other type of image analysis. Indicator image data 342 may comprise information associated with a captured photographic/optical image of a particular indicator (e.g., via photographic image capture unit 324). Capture window data 344 may comprise one or more windows, borders and/or framing indexes for capturing a photographic/optical image of an indicator based on the particular code (e.g., model/serial number) associated with the indicator such that a particular area(s) of interest of the indicator is located and/or contained within the captured image. In some embodiments, imaging module 330 may be configured to initiate image capture only after the indicator has been properly framed/indexed within the capture window.

In FIG. 3, memory 316 also includes capture unit data 346 and location data 348. Capture unit data 346 may comprise information such as an identity of the image capture unit 314 capturing the image/optical data (e.g., embedded unit identifier, IP address reference, etc.) and/or the identity of the image capturing individual (e.g., embedded user ID, user ID log on, unit ID reference, etc.). Location data 348 may comprise information such as the time and date that the image/optical data was captured, the physical location where the image/optical data was generated (e.g., GPS, IP address lookup, etc.).

In the embodiment illustrated in FIG. 3, system 300 also includes a data processing system 350 and a client 352. Data processing system, client 352 and imaging system 310 may configured to communicate with each other (or with select ones thereof), wired and/or wirelessly, via a communication network 354. Data processing system 350 may be located on a server and/or other type of computing processing platform.

In the illustrated embodiment, data processing system 350 includes a processing unit 360 and a storage resource or memory 362. In FIG. 3, memory 362 comprises a detection module 364, indicator code data 366, indicator image data 368 and detection data 370. In FIG. 3, detection module 364 is illustrated as a software program residing in memory 362 and executable by processing unit 360. However, it should be understood that detection module 364 may comprise software, logic and/or executable code for performing various functions as described herein (e.g., residing as software and/or an algorithm running on a processor unit, hardware logic residing in a processor or other type of logic chip, centralized in a single integrated circuit or distributed among different chips in a data processing system).

Indicator code data 366 and indicator image data 368 may comprise information (data and/or image/optical content) received from imaging system 310 via network 354 (e.g., indicator code data 340 and indicator image data 342, respectively). Detection data 370 may comprise information associated with the analysis of such code data 366 and/or image data 368 to derive identification information of the indicator, a status of the corresponding indicator (e.g., armed status, activation status, etc.) and/or various characteristics associated with the indicator (e.g., if activated, a direction of event detection, a duration of event detection, a severity or magnitude of event detection, etc.). For example, in the illustrated embodiment, detection data 370 comprises armed status data 380, activation status data 382, directional activation data 384, duration data 386, severity data 388 and relational data 390. Relational data 390 may comprise information associated with the analysis of code data 366 and/or image data 368 associated with a particular indicator (e.g., based on a particular model/serial number of the indicator). As will be described in greater detail below, detection module 364 analyzes code data 366 and/or image data 368 to derive one or more status indications associated with the particular indicator. For example, different types and/or models of indicators may have different levels of activation that may be derived from image data 368 and that may be dependent on the particular type/model of indicator.

Armed status data 380 may comprise information associated with whether a particular indicator has been armed (i.e., set to detect a particular detection condition). Activation status data 382 may comprise information associated with whether a particular indicator has been activated (i.e., detected and/or is indicating that a particular type of detection event has been realized/detected). Direction activation data 384 may comprise information associated with whether a particular indicator has been subject to an activation/detection event in a particular direction (e.g., receipt of a shock/impact event in a particular direction). Duration status data 386 may comprise information associated with how long or a duration a particular detection event has occurred (e.g., how long a particular temperature condition has been detected). Severity status data 388 may comprise information associated with a severity or degree of the detected event (e.g., indicating a particular temperature or impact level the indicator has detected).

In operation, detection module 364 analyzes code data 366 and/or image data 368 to derive detection data 370. For example, using code data 366, detection module 364 may identify a particular model or type of indicator that is the subject of such analysis. Based on the particular model or type of indicator, detection module 364 may derive one or more of armed status data 380, activation status data 382, directional activation data 384, duration data 386 and severity data 388 based on image data 368. For example, as will be described in greater detail below, information acquired from image data 368 may result in different levels of activation and/or types of activation based on the particular model/type of indicator identified based on code data 366. The status information may then be stored (e.g., retrievable by client 352 via network 354) and/or communicated to client 352 (e.g., via communication network 354). In the illustrated embodiment, detection module 364 and detection data 370 are located remote from imaging system 310;

however, it should be understood that in some embodiments, detection module 364 may reside on imaging system 310, and detection data 370 may be derived by imaging system 310 and thereafter made available to client 352. Client 352 may comprise a computing platform or system associated with a manufacturer/distributor of the indicator, an entity using the indicator, or other entity interested in obtaining status information associated with the indicator. Capture unit data 346 and/or location data 348 may also be received by data processing system 350 from imaging system 310 (e.g., either as standalone data or embedded in other data, such as the image data 332).

Figure 4:
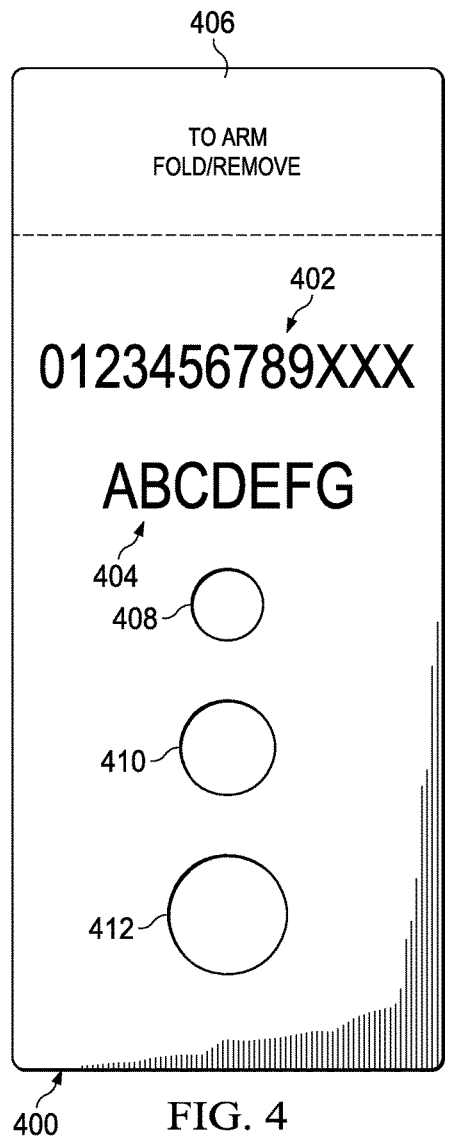
FIG. 4 is a diagram illustrating an embodiment of a temperature indicator with which embodiments of a visual indicator status recognition system and method of the present disclosure may be utilized.

FIG. 4 is a diagram illustrating an embodiment of an indicator 400 in which embodiments of system 300 may be used to provide visual indicator status recognition. In some embodiments of the present disclosure, detection module 364 is used to analyze image/optical data of a product monitoring indicator and determine various types of information such as identity, description and status (e.g. optical character recognition, object recognition, barcode scanning, color/contrast differentiation and/or other types of optical recognition software). Various types of indicators provide a visual indication when specific levels of certain physical phenomena, including but not limited to, temperature, shock, vibration, and humidity, exceed some threshold such that damage may have been caused to the product. A product monitor/indicator may also include its identifying serial number, model number or other type of identification information.

In FIG. 4, indicator 400 is configured to monitor temperature conditions associated with a product to which indicator 400 may be attached and/or associated with. In FIG. 4, indicator 400 is shown in unarmed and non-activated state. Indicator 400 includes a code indicia 402 (e.g., an identifying serial number of the indicator 400) and a code indicia 404 (e.g., a model number of indicator 400). Also shown on indicator 400 is an armed/unarmed indicator 406 and time exposure indicators 408, 410 and 412. The identifying serial number corresponding to code indicia 402 could be represented as, but not limited to, text content, a barcode image, a QR code or other type of indicia. Similarly, the indicator 400 model number corresponding to code indicia 404 could be represented as, but not limited to, text content, a barcode image, a QR code or other type of indicia. The armed/unarmed indicator 406 could be represented as, but not limited to, a designated area whose color and/or other type of indicator element represents the armed/unarmed status of indicator 400 (e.g. indicating whether the indicator is armed and/or enabled for monitoring environmental conditions). In the illustrated embodiment, indicator 406 comprises a tab element that is removable to thereby arm indicator 400; however, it should be understood that other types of devices and/or indications may be contained on a particular indicator that may be used to determine whether the particular indicator has been armed. Time exposure indicators 408, 410 and 412 could be represented as, but not limited to, designated areas in which a color (presence or lack thereof), percent of fill, or other method represents the amount of time that indicator 400 indicator has been subjected to a temperature greater than (or less than) its activation threshold. It should be understood that the time exposure indicator may be otherwise represented (e.g., text-based, color variation, etc.). In FIG. 4, three different indicators 408, 410 and 412 are illustrated with different sizes such that the position of the particular indicator and/or size of indicator represents a duration of temperature detection beyond a threshold activation temperature. In response to detecting a temperature above (or below) the activation temperature, a particular indicator changes color, a color appears within the indicator, text appears, or some other visual indication of activation/detection.

When an image/optical data of indicator 400 is captured and analyzed (e.g., captured by one or more of image capture units 314 and analyzed by detection module 364), the following information may be derived: 1) identifying serial number: 0123456789xxxx; 2) indicator model number: ABCDEFG; 3) indicator armed status: No; and 4) indicator exposure status: 0 minutes. The above information may be derived based on text recognition, code indicia deciphering and/or image analysis of the optical/image data (e.g., color detection, changes in color, absence of color detection, presence of (or absence of) shaded area within a designated indicator region, etc.). For example, in the illustrated embodiment, detection module 364 may analyze image/optical data of indicator 400 to detect that the tab (e.g., indicator 406) is still attached (e.g., by detecting text located on the tab region, an overall dimension/size of indicator 400, the location of an edge of indicator 400 in a region of indicator 406 relative to a location of indicator 408, etc.). Detection module 364 may also analyze image/optical data of indicator 400 to detect whether any of indicators 408, 410 and 412 have a color, have a change in color, or have some other indication associated therewith, such that the particular characteristic (or lack thereof) is used to determine the activation status of indicator 400. Detection module 364 may derive armed status data 380, activation status data 382, directional activation data 384, duration status data 386 and/or severity status data 388 by analyzing the image/optical data and comparing such data to baseline information and/or rules indicating such status/identification information for the indicator (e.g., relational data 390 may comprise information identifying certain status information/identifiers (e.g., a particular color for a region on the indicator, such as indictor 408) that the image/optical data may be compared with and/or analyzed in association with to derive such activation/detection data.

Figure 5:
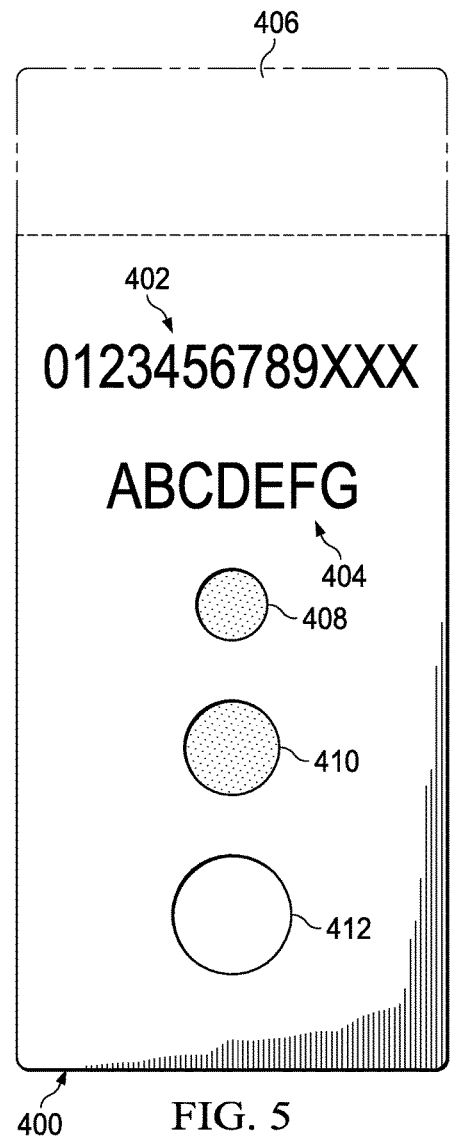
FIG. 5 is a diagram illustrating the temperature indicator of FIG. 4 in an activated state.

FIG. 5 is a diagram illustrating indicator 400 after being armed and activated in response to detecting a monitored event. When an image/optical data of indicator 400 depicted in FIG. 5 is captured and analyzed (e.g., captured by one or more of image capture units 314 and analyzed by detection module 364), the following information would be derived from code indicia 402, code indicia 404, armed/unarmed indicator 406 and time exposure indicators 408/410/412: 1) indicator serial number: 0123456789xxxx; 2) indicator model number: ABCDEFG; 3) indicator armed status: Yes; and 4) indicator exposure status: 15 minutes. As described above, various types of optical/image analysis and recognition methods may be used by detection module 364 to derive the above-referenced information (e.g., text recognition, code deciphering/decryption, detecting the presence or (or absence of) text, color, or other characteristics, detecting a change in a characteristic (e.g., a change in color), etc.).

FIGS. 4 and 5 illustrate that static and variable information may be captured/derived through optical/image recognition and analysis. The static information is represented by the indicator serial number and the indicator model number. The variable information is represented by the indicator armed status and the indicator exposure/indication status. In the case of the indicator armed status, determination may be made by detecting a presence of a particular color, a change in a color, or other type of indication in the designated area of indicator 400. In the case of the indicator exposure status, determination may be made by detecting a presence of a particular color within the designated area of indicator 400, the progression of the color fill of the designated area of indicator 400, based on which indicators have been activated, etc. As an example, color fill of 25% of the area of an indicator area may equate to 15 minutes of exposure. Conversely, 100% fill of the indicator area may equate to 240 minutes of exposure. As described above, the locations of the image/optical data that are analyzed and the results of such analysis may depend on the particular serial/model number of indicator 400. Thus, for one type of indicator, a 25% fill area of an activation indicator may translate to 15 minutes of exposure while the same amount of fill for another indicator may equate to 1 hour of exposure. Thus, in some embodiments, detection module 364 may first derive the serial/model number of the indicator before status as to armed/activation may be derived based on the analyzed image/optical content. Therefore, for example, in the case where a progressive time exposure window/indicator(s) is used (e.g., as depicted in FIGS. 4 and 5), interpretation of the time exposure window/indicator(s) could vary depending upon the indicator serial/model number. In the case where only a single model is used, interpretation of the indicator status window would be based on a preset rule. In the case where multiple models are used, interpretation of the indicator status window could be based on, but not limited to, the following: 1) reading of the model number of the product and then referring to a lookup table or reference equation (e.g., relational data 390) to determine the translation rules and/or 2) reading of the serial number of the indicator and then referring to a lookup table or reference equation (e.g., relational data 390) to determine translation rules.

Further, in some embodiments, an indicator may include multiple and/or a variable severity indicator. For example, a particular indicator may include multiple indicators where different indicators may correspond to different temperature levels experienced by the indicator. Accordingly, image/optical analysis by detection module 364 may identify the activation of different indicators, thereby providing an indication of the severity of the temperature conditions experienced/detected by the indicator.

Figure 6:
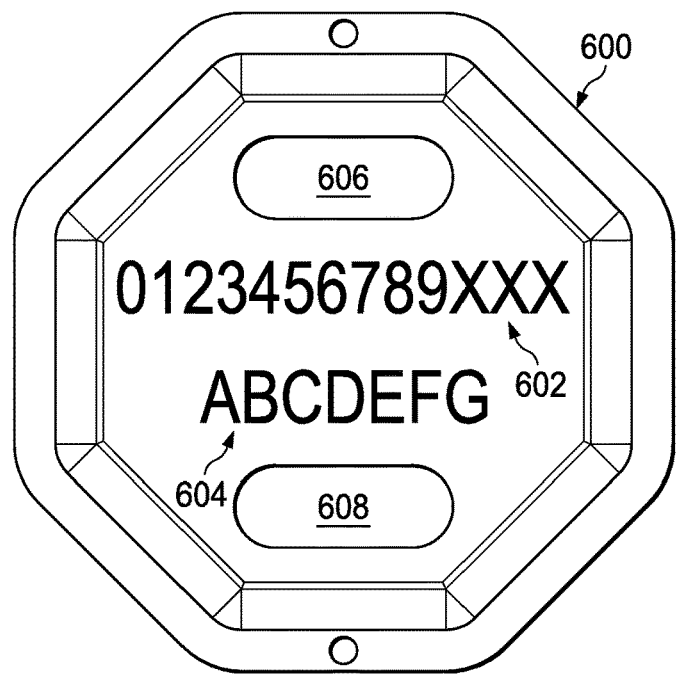
FIG. 6 is a diagram illustrating an embodiment of a shock/impact indicator with which embodiments of a visual indicator status recognition system and method of the present disclosure may be utilized.

FIG. 6 is a diagram illustrating an indicator 600 in which embodiments of system 300 may be used to provide visual indicator status recognition. In FIG. 6, indicator 600 is configured to monitor impact or shock conditions associated with a product to which indicator 600 may be attached. In FIG. 6, indicator 600 includes a code indicia 602 (e.g., an identifying serial number of the indicator 600) and a code indicia 604 (e.g., a model number of indicator 600). Indicator 600 also includes an upper activation indicator 606 and a lower activation indicator 608. Thus, in the illustrated embodiment, indicator 600 is configured to detect impacts/shock events in at least two different directions (e.g., each of indicators 606 and 608 corresponding to a different impact direction). In FIG. 6, indicator 600 is illustrated in a non-activated state.

Thus, when an image/optical data of indicator 600 depicted in FIG. 6 is captured and analyzed (e.g., captured by one or more of image capture units 314 and analyzed by detection module 364), the following information may be derived: 1) indicator serial number: 0123456789xxxx; 2) indicator model number: ABCDEFG; 3) indicator upper window indication: No; and 4) indicator lower window indication: No. The above information may be derived based on text recognition, code indicia deciphering and/or image analysis (e.g., color detection, changes in color, absence of color detection, presence of (or absence of) shaded area within a designated region, etc.).

Figure 7:
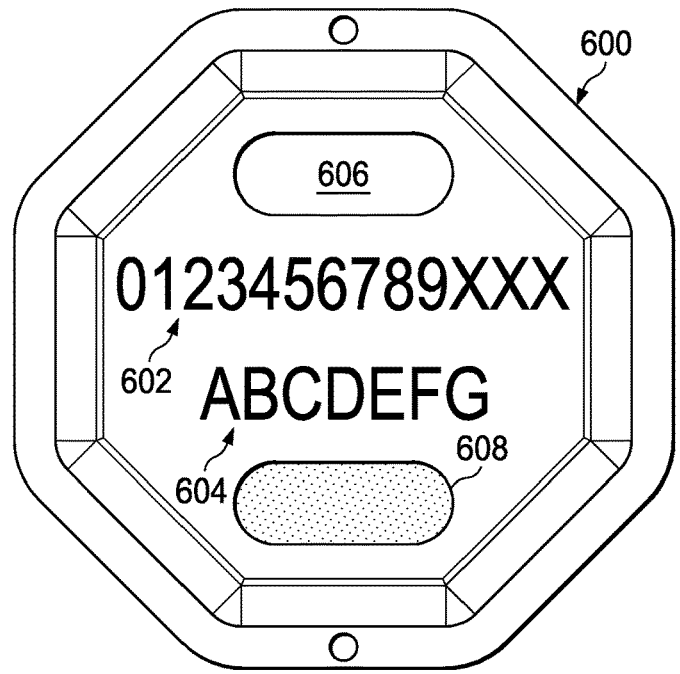
FIG. 7 is a diagram illustrating the shock/impact indicator of FIG. 6 in an activated state.

FIG. 7 is a diagram illustrating indicator 600 in an activated state. As illustrated in FIG. 7, lower activation indicator 608 has changed colors and/or now has a particular color within the region of indicator 608. Thus, when an image/optical data of indicator 600 depicted in FIG. 7 is captured and analyzed (e.g., captured by one or more of image capture units 314 and analyzed by detection module 364), the following information may be derived: 1) indicator serial number: 0123456789xxxx; 2) indicator model number: ABCDEFG; 3) indicator upper window indication: No; and 4) indicator lower window indication: Yes.

Thus, FIGS. 6 and 7 demonstrate that static and variable information is being captured/derived through optical/image recognition. The static information is represented by the indicator serial number and the indicator model number. The variable activation information is represented by the indicator upper activation indicator 606 and the indicator lower activation indicator 608. In the case of the upper and lower activation indicators 606 and 608, activation status may be determined by detecting a color and/or other type of indicator information in the designated window regions/areas of indicators 606 and 608. However, it should be understood that other methods/techniques may be used to derive the activation status (e.g., identification of text within the region of indicators 606 and/or 608, detecting the presence of (or lack of a presence of) a particular color or shading within indicators 606 and/or 608, etc.).

Figure 8:
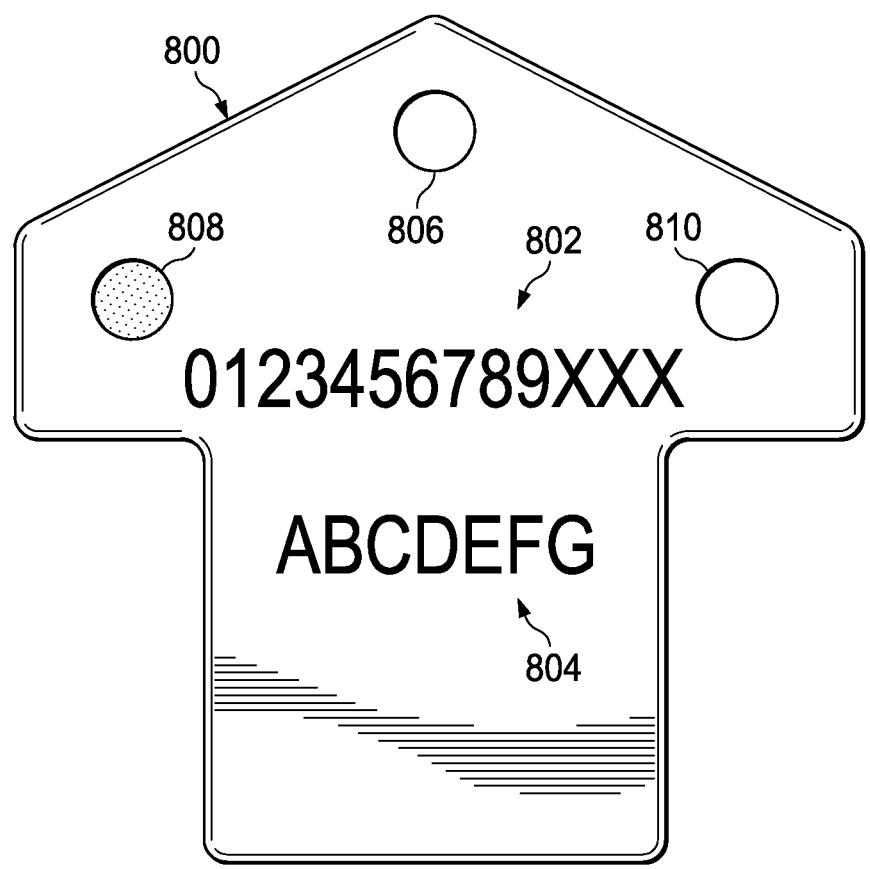
FIG. 8 is a diagram illustrating an embodiment of a tilt indicator with which embodiments of a visual indicator status recognition system and method of the present disclosure may be utilized.

FIG. 8 is a diagram illustrating an indicator 800 in which embodiments of system 300 may be used to provide visual indicator status recognition. In FIG. 8, indicator 800 is configured to monitor tilt events associated with a product to which indicator 800 may be attached. In FIG. 8, indicator 800 includes a code indicia 802 (e.g., an identifying serial number of the indicator 800) and a code indicia 804 (e.g., a model number of indicator 800). Indicator 800 also includes an upper activation indicator 806, a left activation indicator 808 and a right activation indicator 810. Thus, in the illustrated embodiment, indicator 800 is configured to detect tilt events in multiple directions (e.g., each of indicators 806, 808 and 810 corresponding to a different tilt direction/event). In FIG. 8, indicator 800 is illustrated in an activated state (e.g., left activation indicator 808 having a different color located in a region thereof).

Thus, when an image/optical data of indicator 800 depicted in FIG. 8 is captured and analyzed (e.g., captured by one or more of image capture units 314 and analyzed by detection module 364), the following information may be derived: 1) indicator serial number: 0123456789xxxx; 2) indicator model number: ABCDEFG; 3) indicator left window indication: Yes; 4) indicator upper window indication: No; and 5) indicator right window indication: No. Thus, in this example, detection module 364 may identify the model and/or serial number of indicator 800 and, based on the identified model/serial number, analyze the image/optical data to determine whether a left, right or inversion tilt condition has occurred for indicator 800 (e.g., based on the analysis of indicators 806, 808 and 810).

Once an image/optical data has been captured/generated, there are various options by which the data may be processed. For example, in some embodiments, detection module 364 may be located on imaging system 310 (or in close proximity thereto). Responsive to deriving status information by detection module 364, detection module 364 may generate an action as a result of comparing the status data to a pre-configured set of rules used to evaluate the data and/or trigger a response. For example, detection module 364 may generate an alarm on imaging system 310, create a record on imaging system 310, generate a message (e.g., email, SMS, MMS) by imaging system 310 (which may then be sent to client 352, data processing system 350, or elsewhere. It should also be understood that other types of actions may also be undertaken by detection module 364.

In some embodiments, detection module 364 may reside on imaging system 310 (or in close proximity thereto). Detection module 364 may analyze/process the image/optical data and thereafter connect to a remote server or computer system (e.g., data processing system 350) and deliver the derived status information that server/system. The remote server/system would then process the status information and take action determined by a pre-configured set of rules (e.g., sending instructions back to imaging system 310 or elsewhere, record creation in a database, automatic message generation (email, SMS, MMS) and report generation, etc.).

In some embodiments, imaging module 330 captures/acquires the image/optical data and transmits the captured/acquired data to a remote server or computer system (e.g., data processing system 350). Data processing system 350 would then process the image/optical data (e.g., via detection module 364), derive the status information, and take any actions pursuant to a pre-configured set of rules (e.g., sending instructions back to imaging system 310 or elsewhere, record creation in a database, automatic message generation (email, SMS, MMS) and report generation, etc.).

Since temperature and shock data loggers are normally more expensive than indicators, loggers are typically used on larger or more expensive shipments where more than one product is being monitored (at the shipment level). Because indicators are more cost effective, they can be used on individual or lower cost products, enabling a customer to monitor at the unit level rather than shipment or vehicle level. By digitizing indicator status data, a customer may derive audit trails, mapping and reporting analysis, thereby proving new avenues for risk management and decision making.

By capturing and digitizing the static and dynamic indicator status data and matching it to a database stored in an enterprise resource planning or other similar platform, manufacturers can track the product delivered back to the serial number or invoice numbers of the original product, thereby providing the ability to track that environmental integrity (shock, temperature, etc.) in which the product was manufactured was sustained throughout its journey to the customer and/or provide a low cost alternative to prevent the counterfeiting of pharmaceutical or other products (e.g., supports that the product arriving at the customer's doorstep is the same product that was shipped from the manufacturer).

Some indicators ship with a certificate of compliance that states proper testing and storage requirements were met that align with regulatory standards. Because indicator sensitivities align to the cold chain requirements of a specific product, indicators are used to assure compliance with both internal and external regulatory requirements. Embodiments of the present disclosure may be used to verify that elements of the products journey from manufacture to delivery are in compliance with standards set either internally or by regulatory agencies.

Further, time-date stamp and image capture capabilities of the present disclosure can also have an effect on the standard operating procedures for company receiving docks. For example, dock managers may capture image information not only the indicator status, but also the condition of the packaging as it arrives (to support claims for hidden or obvious damage), the bill of lading (to prove that the number of pieces in the shipment match), or even capture an image of the driver delivering the shipment to match with security records (assuring the person who picked up the shipment is the person who delivered it). Any of these elements could support the need for additional documentation in filing a damage claim.

In some embodiments, by utilizing a smart phone or other type of device for image capture (e.g., as imaging system 310), it is much more cost effective for distribution points to capture the status of an indicator and shipment at various positions/locations along a supply chain. And, because the image is captured with a date and time stamp, shipment status checks can occur at any point along the route, tying the chain of custody to the product status at the time of ownership.

Figure 9:
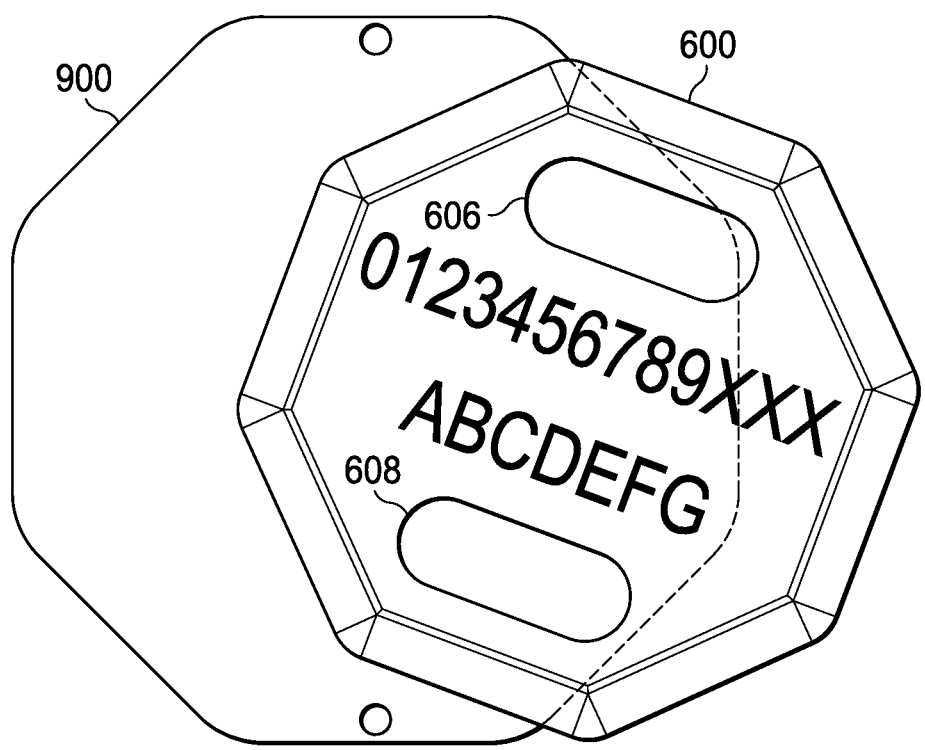
FIG. 9 is a diagram illustrating a capture window utilized by a visual indicator status recognition system and method according to the present disclosure in connection with an impact/shock indicator.

FIG. 9 is a diagram illustrating indicator 600 in connection with a capture window 900 according to an embodiment of the present disclosure. For example, as described above, imaging system 310 may be configured to display and/or otherwise generate a particular capture window 900 (e.g., via capture window data 344) based on the particular indicator identified (e.g., via a serial number, model number or other type of identifying data of the indicator that may be acquired via an initial image/optical data acquired by imaging system 310). In some embodiments, the capture window 900 may be displayed in a viewfinder or other optical element to enable a user or the imaging system to locate indicator 600 within window 900 such that particular areas/regions of interest of indicator 600 (e.g., activation indicators 606 and 608) are located in desired positions within a captured image of indicator 600, thereby facilitating activation status information derivation from the captured image by detection module 364. For example, in the illustrated embodiment, a user may adjust a location/position of indicator 600 and/or adjust a location/position of a particular image capture unit 314 (e.g., rotating slightly and translating) so as to align and/or otherwise locate indicator 600 within capture window 900. It should be understood that in some embodiments, such action may be automatic (e.g., automatically adjusting a location/position/orientation of either the indicator and/or the image capture unit). Further, in some embodiments, after image/optical data acquisition, the image of the indicator may be optically manipulated to position an image of the indicator within window 900 and/or otherwise position desired areas/regions of the indicator in particular locations for detection/analysis.

Figure 10:
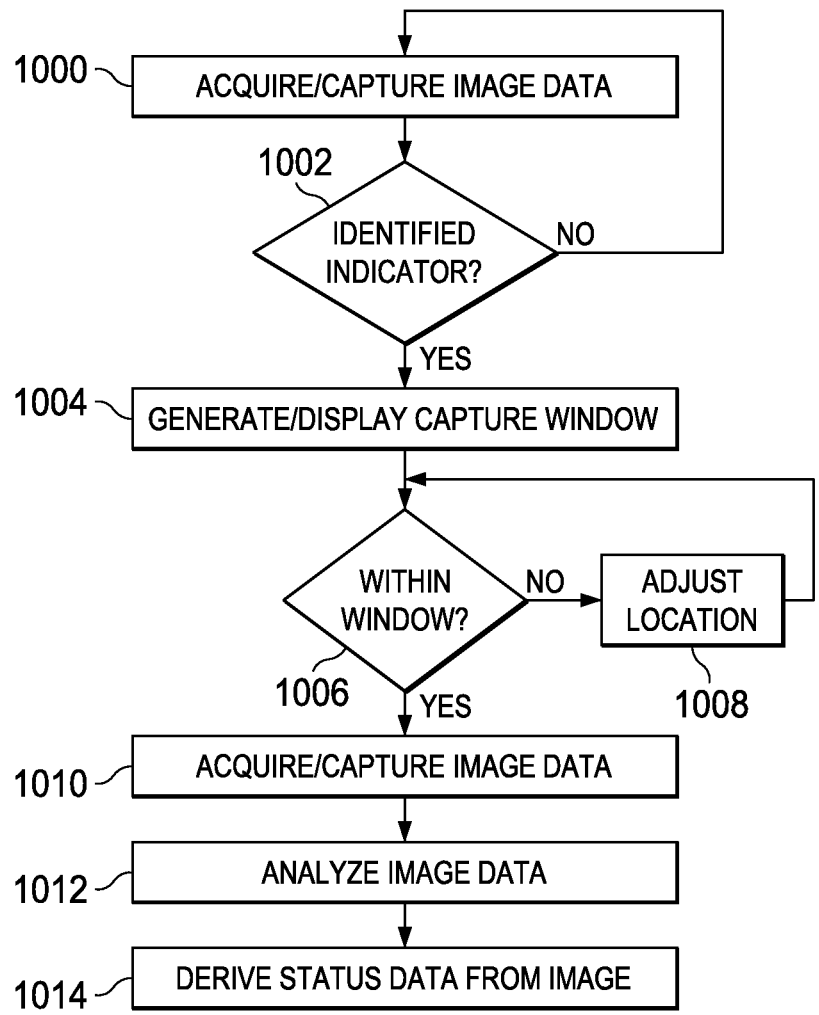
FIG. 10 is a flow diagram illustrating an embodiment of a visual indicator status recognition method according to the present disclosure.

FIG. 10 is a flow diagram illustrating an embodiment of a method for visual indicator status recognition. The method begins at block 1000, where an initial image/optical data is acquired of an indicator. For example, the initial image/optical data may comprise a barcode, QR code, a photographic image from which a serial or model number may be derived, etc. At decisional block 1002, a determination is made whether the indicator may be identified from the captured image/optical data. For example, in some embodiments, imaging system 310 may be configured to verify the acquisition of model number, serial number and/or another type of indicator code data 340 (or verify that such information may be derived from the captured image/optical data, such as verifying the quality of the captured image/optical data to enable text recognition of content within the image/optical data). If not, the method may return to block 1000. If so, the method proceeds to block 1004, where a capture window may be identified (e.g., from capture window data 344) and displayed/generated. At decisional block 1006, a determination is made whether the particular indicator is located within the capture window. If not, the method proceeds to block 1008, where the user of imaging system 310 may be instructed and/or prompted to locate the indicator within the capture window. If the indicator is located within the capture window, the method proceeds to block 1010.

At block 1010, imaging system 310 acquires another image/optical data of the indicator. At block 1012, detection module 364 analyzes the image/optical data, and at block 1014, detection module 364 derives activation status information or other types of information from the image/optical data (e.g., armed status, activation status, activation direction and/or severity, etc.).

It should be understood that in some embodiments, a single image/optical data may be acquired by imaging system that may enable static and variable status information to be derived therefrom. For example, in some embodiments, from a single photographic image, code data 340 (e.g., a model and/or serial number of the indicator) may be derived (e.g., via text recognition or otherwise) and variable activation status information may also be derived therefrom (e.g., via detection module 364 by analyzing the image).

Thus, embodiments of the present disclosure enable visual indicator status information to be captured/digitized to enable environmental conditions monitored by such indicator to be monitored/tracked and/or readily available to a customer or other entity. For example, in some embodiments, static and dynamic/variable status information may be derived from captured image/optical data of the indicator. The indicator information may be processed locally and/or remotely relative to the indicator.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A visual indicator recognition system, comprising:
    a camera configured to capture an image of an indicator device; and
    a detection circuit executable by a processing unit to:
        derive at least one of a model number and a serial number of the indicator device from the image;
        based on the at least one of the model number and the serial number, access relational data to determine a location on the indicator device of a dynamic indicating region for a type of indicator device indicated by the at least one of the model number and the serial number, the at least one of the model number and the serial number indicative of a physical phenomenon measured by the type of the indicator device;
        optically manipulate the image to position a select area of the image in a particular location based on the location of the indicating region; and
        analyze the select area to derive status information of the indicator device corresponding to the indicating region.

2. The system of claim 1, wherein the status information includes an activation status of the indicator device.

3. The system of claim 1, wherein the status information includes an armed status of the indicator device.

4. The system of claim 1, wherein the status information includes an activation duration of the indicator device.

5. The system of claim 1, wherein the detection circuit is configured to derive the at least one of the model number and the serial number from a barcode in the image.

6. The system of claim 1, wherein the detection circuit is configured to perform character recognition processing to derive the at least one of the model number and the serial number from the image.

7. The system of claim 1, wherein the detection circuit is configured to derive the status information based on the relational data.

8. A visual indicator recognition system, comprising:
    a camera configured to capture an image of an indicator device; and
    a detection circuit executable by a processing unit to:
        derive at least one of a model number and a serial number of the indicator device from the image;
        based on the at least one of the model number and the serial number, access relational data to identify a capture window for a type of indicator device indicated by the at least one of the model number and the serial number, the at least one of the model number and the serial number indicative of a physical phenomenon measured by the type of the indicator device;
        optically manipulate the image to position the indicator device depicted in the image within the capture window; and
        analyze the image to derive status information of the indicator device.

9. The system of claim 8, wherein the detection circuit is configured to derive the status information based on the relational data.

10. The system of claim 9, wherein the detection circuit is configured to determine a translation rule from the relational data.

11. The system of claim 8, wherein the capture window defines a position for the indicator device to locate an indicating region of the indicator device in a particular location.

12. The system of claim 8, wherein the detection circuit is configured to derive the at least one of the model number and the serial number from a barcode in the image.

13. The system of claim 8, wherein the detection circuit is configured to perform character recognition processing to derive the at least one of the model number and the serial number from the image.

14. The system of claim 8, wherein the detection circuit is configured to analyze at least two different and spaced apart locations in the image to acquire the status information of the indicator device corresponding to respective indicating regions of the indictor device.

15. A method, comprising:
capturing an image of an indicator device;
deriving at least one of a model number and a serial number of the indicator device from the image;
based on the at least one of the model number and the serial number, identifying a capture window for a type of indicator device indicated by the at least one of the model number and the serial number, the at least one of the model number and the serial number indicative of a physical phenomenon measured by the type of the indicator device;
optically manipulating the image to position the indicator device depicted in the image within the capture window; and
analyzing the image to derive status information of the indicator device.

16. The method of claim 15, further comprising accessing relational data to identify the capture window based on the at least one of the model number and the serial number.

17. The method of claim 15, further comprising accessing relational data to identify a translation rule based on the at least one of the model number and the serial number.

18. The method of claim 15, further comprising configuring the capture window to define a position for the indicator device to locate an indicating region of the indicator device in a particular location.

19. The method of claim 15, further comprising deriving the at least one of the model number and the serial number from a barcode in the image.

20. The method of claim 15, further comprising performing character recognition processing to derive the at least one of the model number and the serial number from the image.

* * * * *